(12) United States Patent
Sommermeyer et al.

(10) Patent No.: US 12,173,318 B2
(45) Date of Patent: Dec. 24, 2024

(54) ENRICHMENT OF T CELLS USING AN ANTI-Cβ ANTIBODY

(71) Applicant: MEDIGENE IMMUNOTHERAPIES GMBH, Planegg-Martinsried (DE)

(72) Inventors: Daniel Sommermeyer, Munich (DE); Slavoljub Milosevic, Munich (DE); Anna Schleicher, Munich (DE)

(73) Assignee: MEDIGENE IMMUNOTHERAPIES GMBH, Planegg-Martinsried (DE)

( * ) Notice: Subject to any disclaimer, the term of this patent is extended or adjusted under 35 U.S.C. 154(b) by 0 days.

(21) Appl. No.: 18/020,303

(22) PCT Filed: Aug. 17, 2021

(86) PCT No.: PCT/EP2021/072792
§ 371 (c)(1),
(2) Date: Feb. 8, 2023

(87) PCT Pub. No.: WO2022/038115
PCT Pub. Date: Feb. 24, 2022

(65) Prior Publication Data
US 2023/0287345 A1 Sep. 14, 2023

(30) Foreign Application Priority Data
Aug. 18, 2020 (EP) .................................. 20191622

(51) Int. Cl.
*C12N 5/0783* (2010.01)
*C07K 14/725* (2006.01)

(52) U.S. Cl.
CPC ........ *C12N 5/0636* (2013.01); *C07K 14/7051* (2013.01); *C12N 2501/505* (2013.01)

(58) Field of Classification Search
CPC ............ C12N 5/0636; C12N 2501/505; C12N 2510/00; C12N 5/0087; C12N 5/0638; C07K 14/7051; A61K 39/0011; A61K 39/4611; A61K 39/4632; A61K 39/4644
See application file for complete search history.

(56) References Cited

FOREIGN PATENT DOCUMENTS

| WO | WO-2015/132598 A1 | 9/2015 | |
|---|---|---|---|
| WO | WO-2019138217 A1 * | 7/2019 | ............. A61K 35/17 |
| WO | WO-2020/089644 A1 | 5/2020 | |

OTHER PUBLICATIONS

Clauss et al., "Efficient non-viral T-cell engineering by *sleeping beauty* minicircles diminishing DNA toxicity and miRNAs silencing the endogenous T-cell receptors" Hum Gen Ther. 29(5): 569-84 (2018).

International Search Report and Written Opinion for International Patent Application No. PCT/EP2021/072792 dated Dec. 22, 2021 (16 pages).

* cited by examiner

*Primary Examiner* — Amy E Juedes
*Assistant Examiner* — Brian Hartnett
(74) *Attorney, Agent, or Firm* — Clark & Elbing LLP

(57) ABSTRACT

The present invention describes methods and uses of antibodies targeting the Cβ1 or the Cβ2 chain of a TCR, in particular an anti-Cβ1 antibody, for enrichment of T cells expressing a desired antigen-specific recombinant T cell receptor (TCR).

16 Claims, 11 Drawing Sheets

Figure 1:
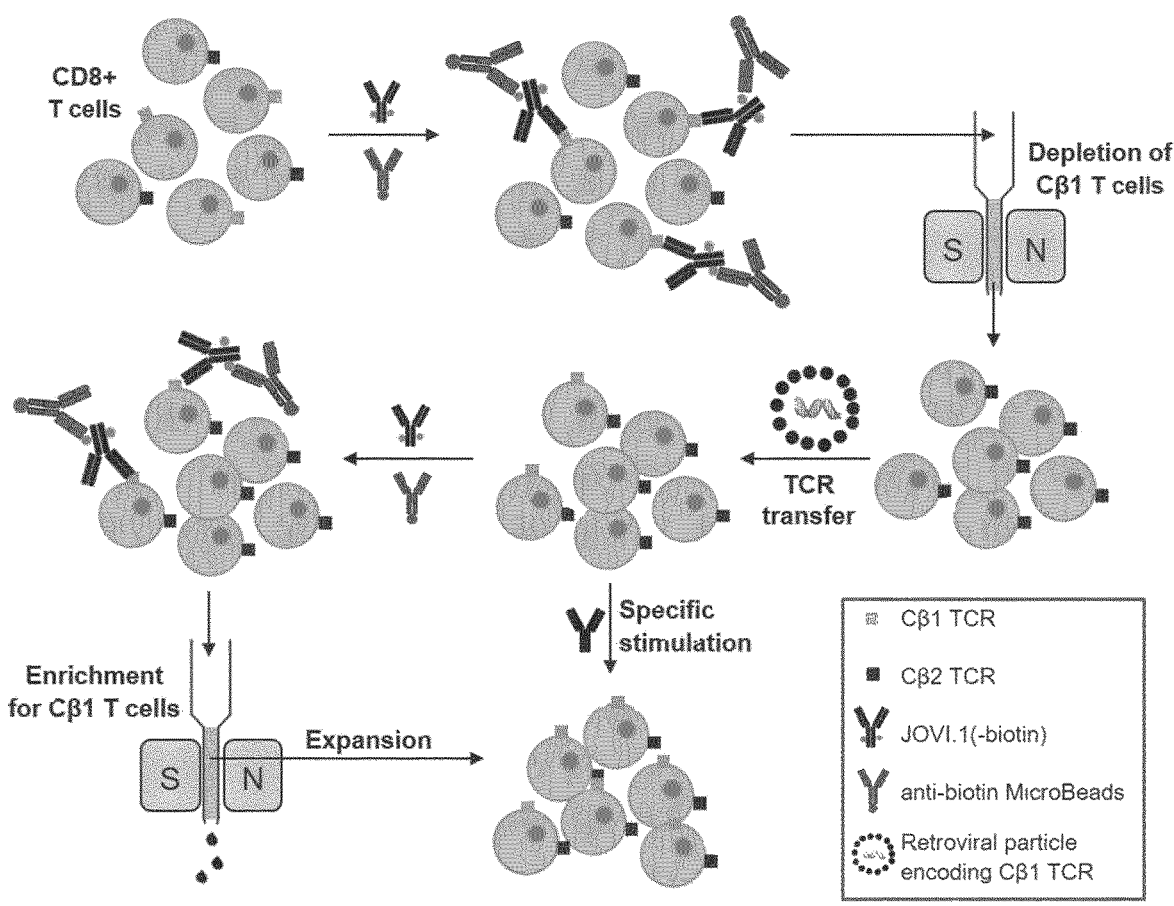

Specification includes a Sequence Listing.

ENRICHMENT OF T CELLS USING AN ANTI-Cβ ANTIBODY

FIELD OF THE INVENTION

The present invention describes methods and uses of antibodies targeting the Cβ1 or the Cβ2 chain of a T cell receptor (TCR), in particular an anti-Cβ1 antibody, for enrichment and stimulation of T cells expressing a desired antigen-specific recombinant T cell receptor.

BACKGROUND OF THE INVENTION

T lymphocytes are part of the adaptive immune response and originate from hematopoietic stem cells located in the bone marrow. T lymphocytes express a unique antigen binding receptor on their membrane, the T cell receptor (TCR), which recognizes antigens in association with major histocompatibility complex (MHC) molecules.

With their central role in the immune system, T cells typically provide protection from pathogens or malignant cells. Each T cell expresses a single form of a T cell receptor, a structure which is used by the T cell to recognize infected or altered cells.

The concept of immunotherapy is based on the specificity of the adaptive immune response for the recognition and elimination of pathogens as well as tumor cells. The aim of a successful immunotherapy is the manipulation or reprogramming of the patient's immune response in order to specifically target pathogen-infected cells or tumor cells for destruction by the immune system.

Therapeutic approaches used to reprogram the immune system in the treatment of infectious diseases and cancer include active immunotherapy comprising the use of vaccination strategies, including dendritic cell (DC) vaccines, as well as passive immunotherapy comprising the application of specific antibodies or genetically engineered lymphocytes or the adoptive transfer of T cells specifically recognizing target antigens displayed by pathogen-infected cells or cancers.

The principle of adoptive T cell transfer is based on the ex vivo expansion of autologous or allogeneic target-specific T lymphocytes and the subsequent re-infusion into patients. Cancer regression in patients suffering from metastatic melanoma has been observed after the transfer of ex vivo expanded autologous tumor-infiltrating lymphocytes (TILs). The drawback of this therapeutic approach is the requirement for pre-existing tumor-reactive cells that need to be isolated from every individual patient as well as the difficult detection of TILs for cancers other than melanoma. Therefore, other methods were developed that focus on the genetic modification of T cells isolated from patients. These genetically engineered T cells can for example be created by transduction of autologous T cells with the a and B chains of target-specific TCRs, i.e. with recombinant TCRs. Likewise, there have also been successful treatments of life-threatening infections with adoptive transfer of virus-specific T cells, for example to combat Epstein-Barr-Virus- and Cytomegalovirus-driven infections in immune-compromised individuals. This is a pathway that could also be pursued for treatment of COVID-19 patients in dire situations.

An approach, as developed by Wilde et al. in 2009 and described in WO 2007/017201, allows the isolation of allo-restricted peptide-specific T cells using autologous DCs co-transfected with RNA species encoding both the target antigen and a selected allogeneic MHC molecule. By co-culturing autologous T cells with DCs presenting self-peptide/allo-MHC complexes, high-avidity T cells that recognize self-antigens can be obtained (Wilde et al., 2009, Dendritic cells pulsed with RNA encoding allogeneic MHC and antigen induce T cells with superior antitumor activity and higher TCR functional avidity. Blood, 114 (10), 2131-9). Likewise, T cells and their corresponding TCRs can be obtained by culturing autologous T cells and autologous DCs expressing the human leukocyte antigens (HLAs) of choice and loaded with foreign antigens, such as those expressed by pathogenic viruses in infected cells. Because T cell cultivation and expansion of individual T cell clones is laborious and requires repeated rounds of re-stimulation, it is an advantage to rapidly acquire the sequences of the TCRs at an early time point in order to allow their rapid characterization by introducing them into recipient peripheral blood lymphocyte-containing T cells. This allows the characterization of the TCRs regarding antigen specificity, peptide/MHC-avidity and functionality before they are selected for further use in therapeutic applications in patients.

However, since a T cell already comprises an endogenous TCR, selection of T cells in which a desired recombinant TCR has successfully been introduced and expressed at the cell surface remains difficult. So far, this has been achieved either using antigen-driven selection (e.g. with the use of peptide/MHC multimers), of through use of engineered tags (e.g. addition of a Strep-tag) that are introduced with the recombinant TCR sequence. Antigen-driven selection is tedious and does not permit a universal screening protocol, since each TCR, which targets a different antigen presented by a potentially different HLA molecule, requires a specific enrichment protocol. Selection tags which are engineered into the TCR might cause unwanted immune responses against the tag.

Thus, straight-forward strategies are needed for the enrichment of T cells expressing a recombinant TCR that are independent of antigen specificity and do not require use of engineered selection tags that must be artificially introduced into the TCR.

In α:β T cells, the specificity of a TCR is defined by two chains, namely the alpha (α) chain and the beta (β) chain. Each chain is composed of two domains, namely the variable region and the constant region. TCR chains are formed by the genomic recombination of a single variable (V), diversity (D, only for beta chains), joining (J) and constant (C) segment.

In humans, the genome contains two highly homologous and functionally equivalent C loci for the beta chain (TRBC) termed TRBC1 and TRBC2 (wherein the locus is located on Chr7:q34). Accordingly, the beta-chain constant region of a TCR in a T cell is either coded by TRBC1 or TRBC2, wherein the two regions differ in 4 amino acids. The beta-chain regions coded by either TRBC1 or TRBC2 are termed Cβ1 (C beta 1) and Cβ2 (C beta 2). The amino acid sequence of the Cβ1 chain is set out in SEQ ID NO: 9. The amino acid sequence of the Cβ2 chain is set out in SEQ ID NO: 10.

In a given wild-type TCR, the beta-chain region variants can be exchanged with each other without changing the specificity or functional avidity of the TCR. Thus, it is possible to switch from a Cβ1 to a Cβ2 domain (or vice-versa) in the recombinant TCR to be introduced and expressed in the selected recipient T cells.

OBJECTIVES AND SUMMARY OF THE INVENTION

The present invention provides strategies for generating a T cell population enriched for T cells expressing a recombinant TCR, comprising the steps:

a) Incubating a composition comprising T cells with an anti-Cβ antibody selected from the group consisting of an anti-Cβ1 antibody and anti-Cβ2 antibody,
b) Depleting T cells bound to the anti-Cβ antibody,
c) Introducing into the T cell population obtained in step b) a recombinant TCR containing a Cβ chain to which the anti-Cβ antibody binds,
d) Enriching T cells expressing the recombinant TCR in the population obtained in step c) using the anti-Cβ antibody.

In some embodiments the present invention provides strategies for generating a T cell population enriched for T cells expressing a recombinant TCR, comprising the steps:
a) Incubating a composition comprising T cells with an anti-Cβ1 antibody,
b) Depleting T cells bound to the anti-Cβ1 antibody,
c) Introducing into the T cell population obtained in step b) a recombinant TCR containing a Cβ1 chain,
d) Enriching T cells expressing the recombinant TCR in the population obtained in step c) using the anti-Cβ1 antibody.

By depletion of T cells containing a Cβ1 chain from the starting T cell population and subsequently introducing a desired recombinant TCR containing a Cβ1 chain into the depleted T cell population, it is possible to specifically select, isolate and enrich the T cells containing the desired recombinant TCR, based on a naturally inherent TCR Cβ1 chain which is used as a universal marker to allow antigen-independent selection. Alternatively, in the recombinant TCR the Cβ2 chain can be exchanged for the Cβ1 chain so that the system is easy adaptable to any TCR. Thereby, a universal, cost- and time-saving approach is provided for generating a T cell population enriched for T cells expressing a recombinant TCR of choice.

By this method, the introduction of a selection tag which is not present naturally in the TCR, such as a Strep-Tag, can be omitted. The TCR Cβ1 chain that is used for selection is a natural part of TCRs and therefore no manipulation of the TCR is necessary to allow selection of the TCR-expressing T cells. As already mentioned before, in the recombinant TCR, the Cβ2 chain may be exchanged for the Cβ1 chain. Since the exchange of the Cβ2 chain by the Cβ1 only generates naturally occurring sequences, potential neoepitopes that could generate an unwanted unspecific immune response can be also avoided. Thereby, potential unwanted immune responses directed against foreign selection tags artificially engineered into the TCR can be avoided.

The skilled in the art understands that the method explained in detail for the anti-Cβ1 antibody can also be applied to an anti-Cβ2 antibody (i.e. an antibody binds to Cβ2 and that does substantially not bind to Cβ1) which can be used for the enrichment of an a TCR containing a Cβ2 chain.

In addition, since the enrichment is dependent on a naturally occurring structural feature of TCRs, which is independent of target specificity encoded by the variable region of the TCR, the claimed method allows for a universal enrichment for any and all TCRs comprising a Cβ1 chain, independent of their antigen-specificities.

Thus, in a specific embodiment the recombinant TCR does not contain any engineered selection tag which is not present in a natural TCR (e.g. the recombinant TCR does not contain a Strep-tag).

In some embodiments at least 60%, preferably at least 70%, more preferably at least 80%, most preferably at least 90% of the T cell population obtained in step d) express the recombinant TCR.

This means that after the enrichment of step d) at least 60%, preferably at least 70%, more preferably at least 80%, most preferably at least 90% of T cells of the total population obtained after step d) express the recombinant TCR.

In specific embodiments step d) comprises the steps
Incubating the cells with an anti-Cβ1 antibody, and
Isolating the T cells bound to the anti-Cβ1 antibody.
Optionally step d) further comprises the step of
Expanding the isolated T cells.
Alternatively step d) may comprise the step
Incubating the cells with an anti-Cβ1 antibody, wherein the incubation with the anti-Cβ1 antibody stimulates proliferation of T cells expressing the TCR containing a Cβ1 chain.

Typically, in step c) a retroviral particle is used for the introduction of the recombinant TCR.

Usually, the composition of T cells comprises a population of T cells expressing a Cβ1 chain and a population of T cells expressing a Cβ2 chain.

The composition comprising T cells may be obtained from a human. In some embodiments, the composition of T cells comprises peripheral blood mononuclear cells (PBMCs). The T cell may be a CD4+ or a CD8+ T cell. Preferably, the T cell is a CD8+ T-cell.

Typically, the recombinant TCR has a desired antigen-specificity.

In specific embodiments the anti-Cβ1 antibody of step a) is biotinylated. Then the selection is carried out with a molecule having an anti-biotin binding domain, such as MicroBeads.

Thus, in a preferred embodiment, the anti-Cβ1 antibody is biotinylated and anti-biotin MicroBeads are used for isolating the T cells bound to the anti-Cβ1 antibody.

The anti-Cβ1 antibody may be a monoclonal mouse IgG2a antibody. In a preferred embodiment the anti-Cβ1 antibody is the JOVI.1 antibody, which is commercially available, e.g. from SantaCruz Biotechnology or ThermoFisher Scientific.

Another aspect refers to the use of an anti-Cβ1 antibody for the enrichment of T cells expressing a recombinant TCR.

Also kits for carrying out the method of the invention are contemplated.

FIGURE LEGENDS

FIG. 1: Concept using JOVI.1 monoclonal antibody to enrich and expand recombinant TCR-expressing T cells. Cβ1-positive T cells can be labeled with a combination of JOVI.1-biotin antibody and anti-biotin MicroBeads and depleted by MACS (Magnetic-activated cell sorting). The Cβ1-negative T cells can then be transduced with a recombinant TCR containing Cβ1. TCR-expressing transgenic Cβ1-positive T cells can be labeled with a combination of JOVI.1-biotin antibody and anti-biotin MicroBeads and enriched by MACS or they can be enriched by the specific stimulation with JOVI.1 monoclonal antibody.

Figure 2:
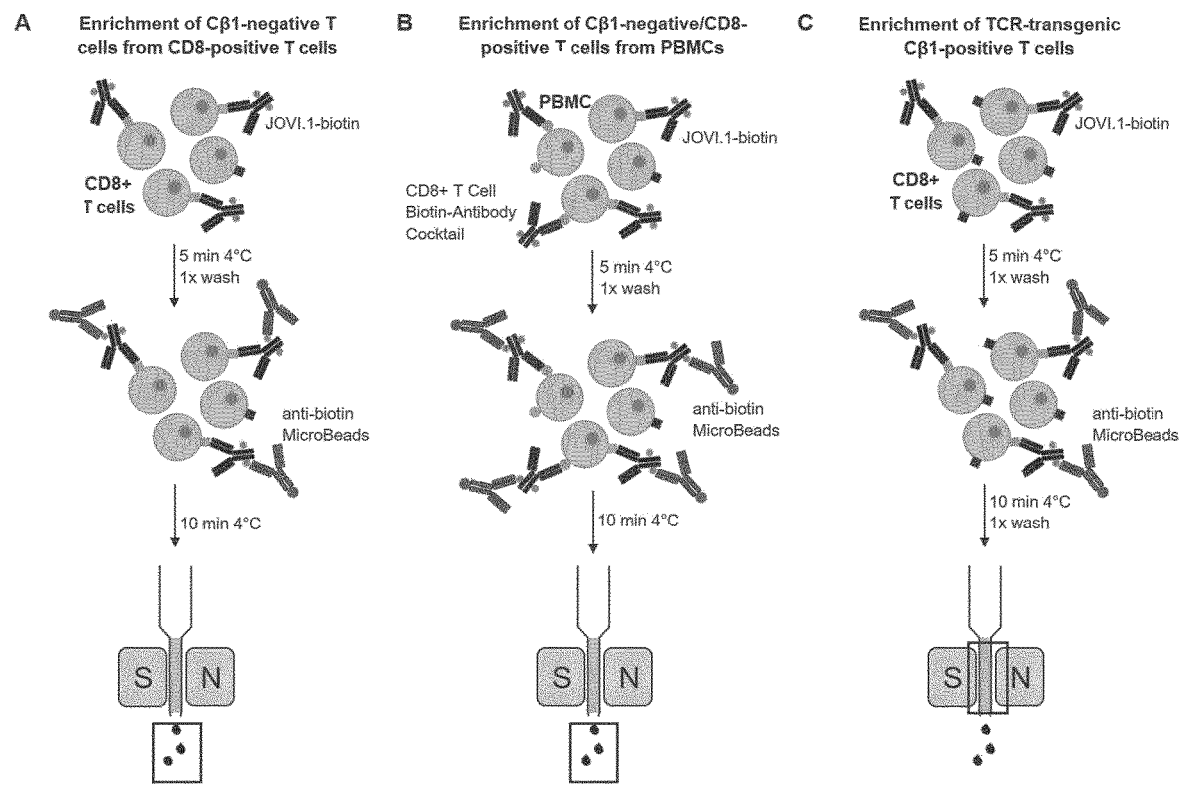

FIG. 2: Schematic of protocols to deplete or enrich Cβ1-positive T cells. (A) Depletion of Cβ1-positive T cells from CD8+ T cells. CD8+ T cells are incubated with JOVI.1-biotin antibody for 5 min at 4° C., washed with MACS buffer, incubated for 10 min at 4° C. with anti-biotin MicroBeads and loaded on a MACS column. The flow through contains the Cβ1-depleted CD8+ T cells. (B) Depletion of Cβ1-positive and enrichment for CD8+ T cells from PBMCs. PBMCs are incubated with JOVI.1-biotin antibody and the "CD8+ T Cell Biotin-Antibody Cocktail" (Miltenyi) for 5 min at 4° C., washed with MACS buffer, incubated for 10 min at 4° C. with anti-biotin MicroBeads (Miltenyi) and loaded on a MACS column. The flow through contains the Cβ1-depleted CD8-enriched T cells. (C) Enrichment of Cβ1-positive TCR-transgenic T cells. T cells are incubated with JOVI.1-biotin antibody for 5 min at 4° C., washed with MACS buffer, incubated for 10 min at 4° C. with anti-biotin MicroBeads and loaded on a MACS column. Cβ1-positive TCR-transgenic T cells are enriched in the MACS column and can be eluted after removal of the magnet.

Figure 3:
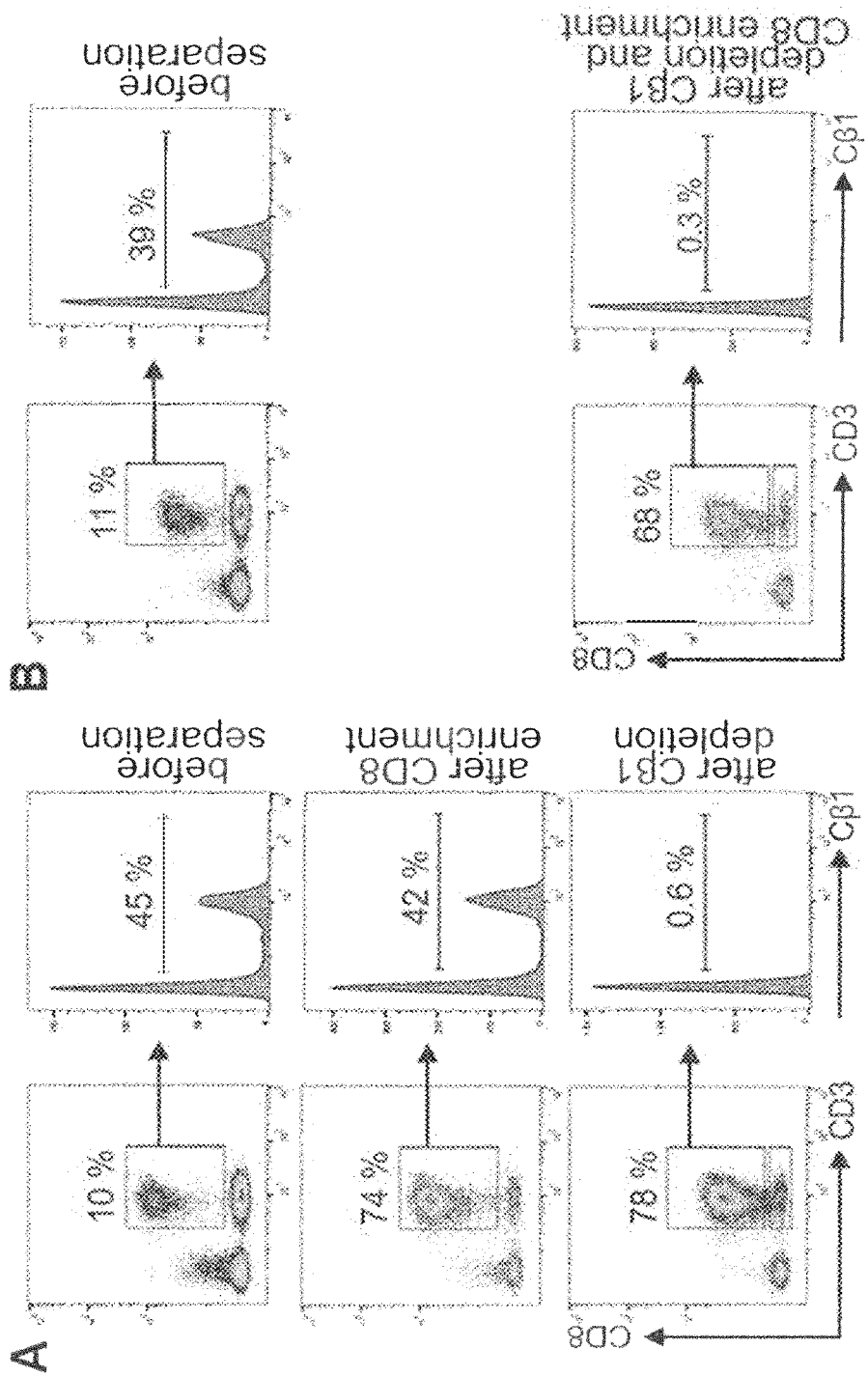

FIG. 3: Enrichment of Cβ1-negative/CD8-positive T cells from CD8+ T cells or PBMCs. (A) CD8+ T cells were enriched from PBMCs by a standard protocol and then Cβ1-positive T cells were depleted. Samples were analyzed by flow cytometry for CD3, CD8 and Cβ1 before enrichment, after CD8 enrichment and after Cβ1 depletion. (B) Cβ1-depleted CD8-enriched T cells were isolated in one step from PBMCs. Samples were analyzed by flow cytometry for CD3, CD8 and Cβ1 before enrichment and after Cβ1 depletion and CD8 enrichment.

Figure 4:
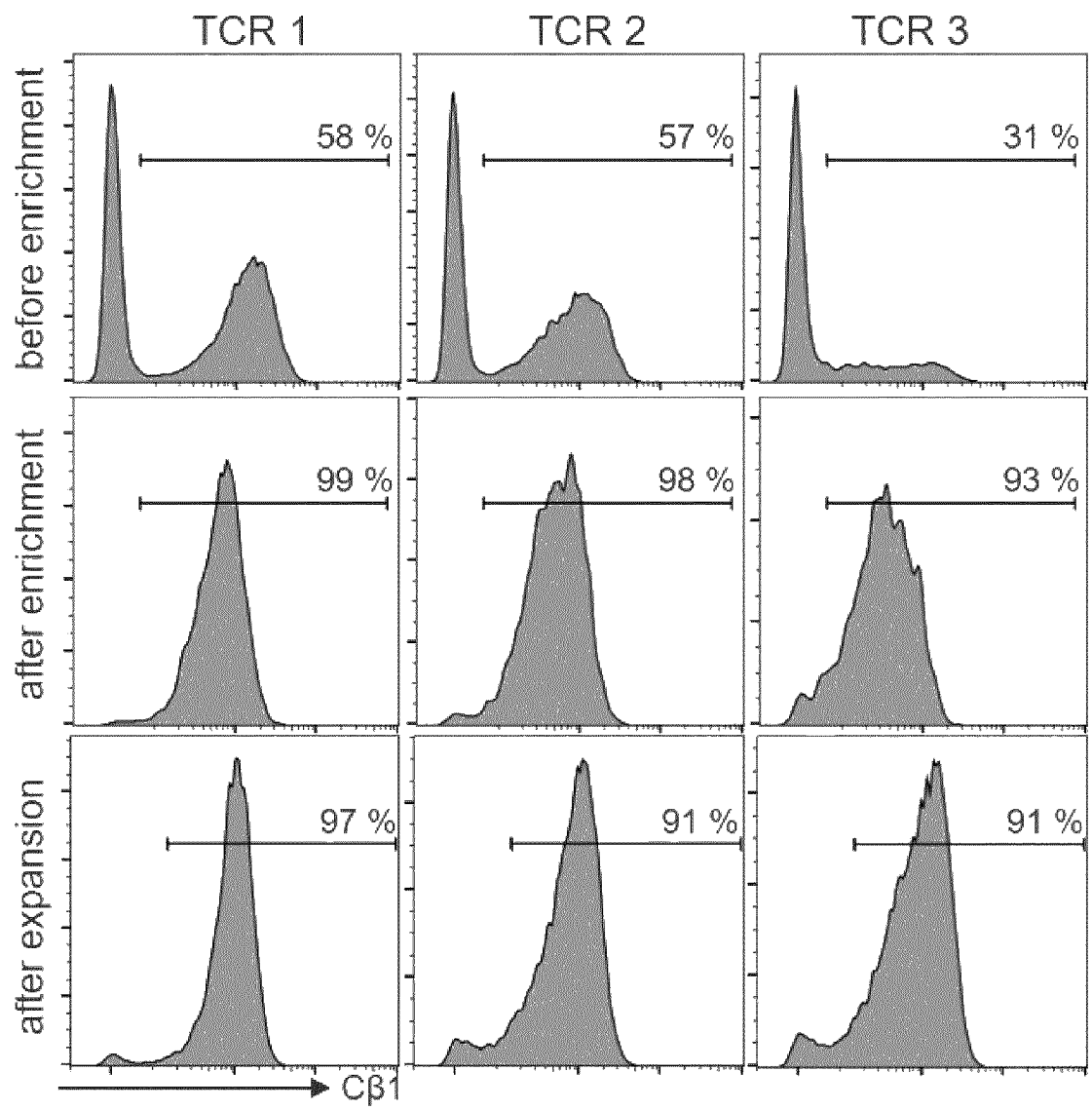

FIG. 4: MACS enrichment of Cβ1-positive TCR-transgenic T cells. Cβ1-depleted CD8-enriched T cells were transduced with three different recombinant TCRs. TCR-transgenic T cells were enriched by MACS using JOVI.1 antibody and expanded. T cells were analyzed by flow cytometry for Cβ1 expression before enrichment, after enrichment and after expansion.

Figure 5:
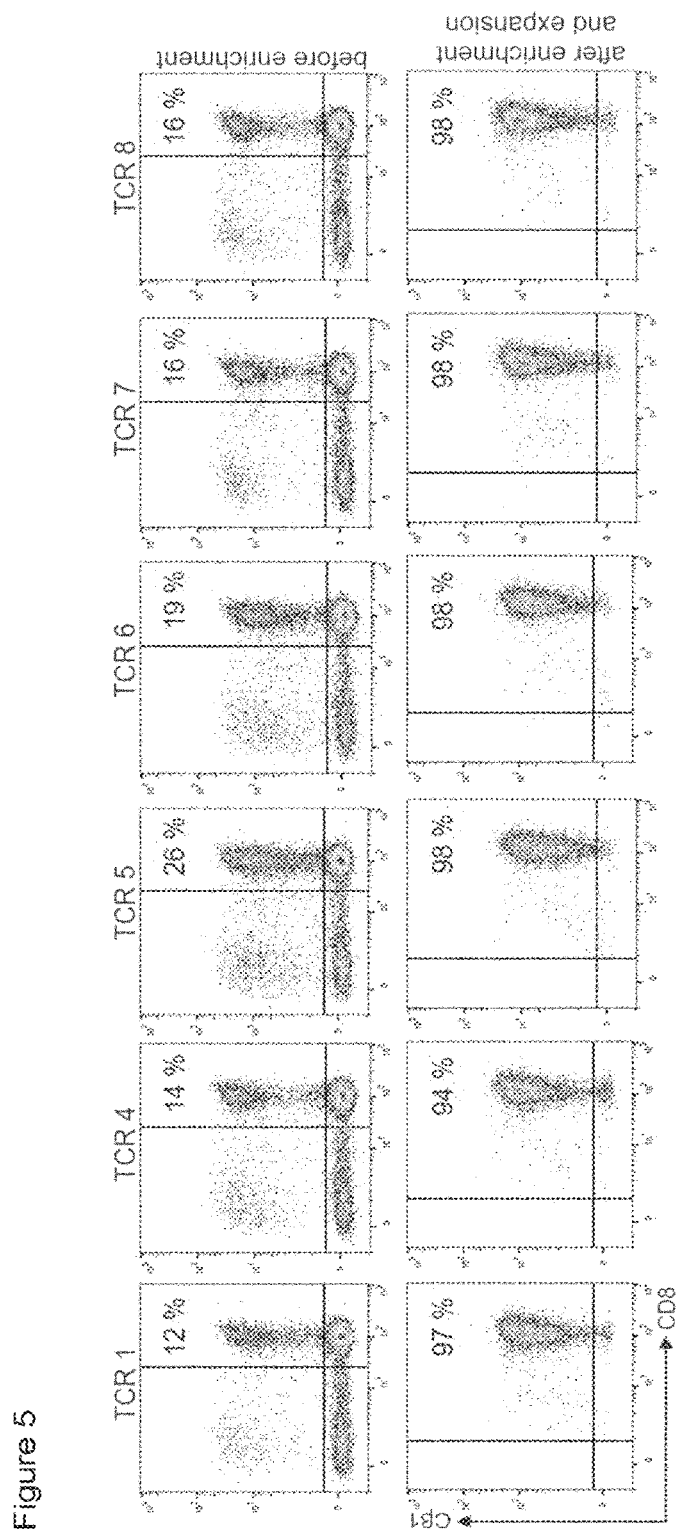

FIG. 5: FACS enrichment of Cβ1-positive CD8+ TCR-transgenic T cells. Cβ1-depleted CD8-enriched T cells were transduced with six different recombinant TCRs. TCR-transgenic T cells were enriched by FACS using JOVI.1 antibody and CD8 antibody and expanded. T cells were analyzed by flow cytometry for Cβ1 and CD8 expression before enrichment and after enrichment and expansion.

Figure 6:
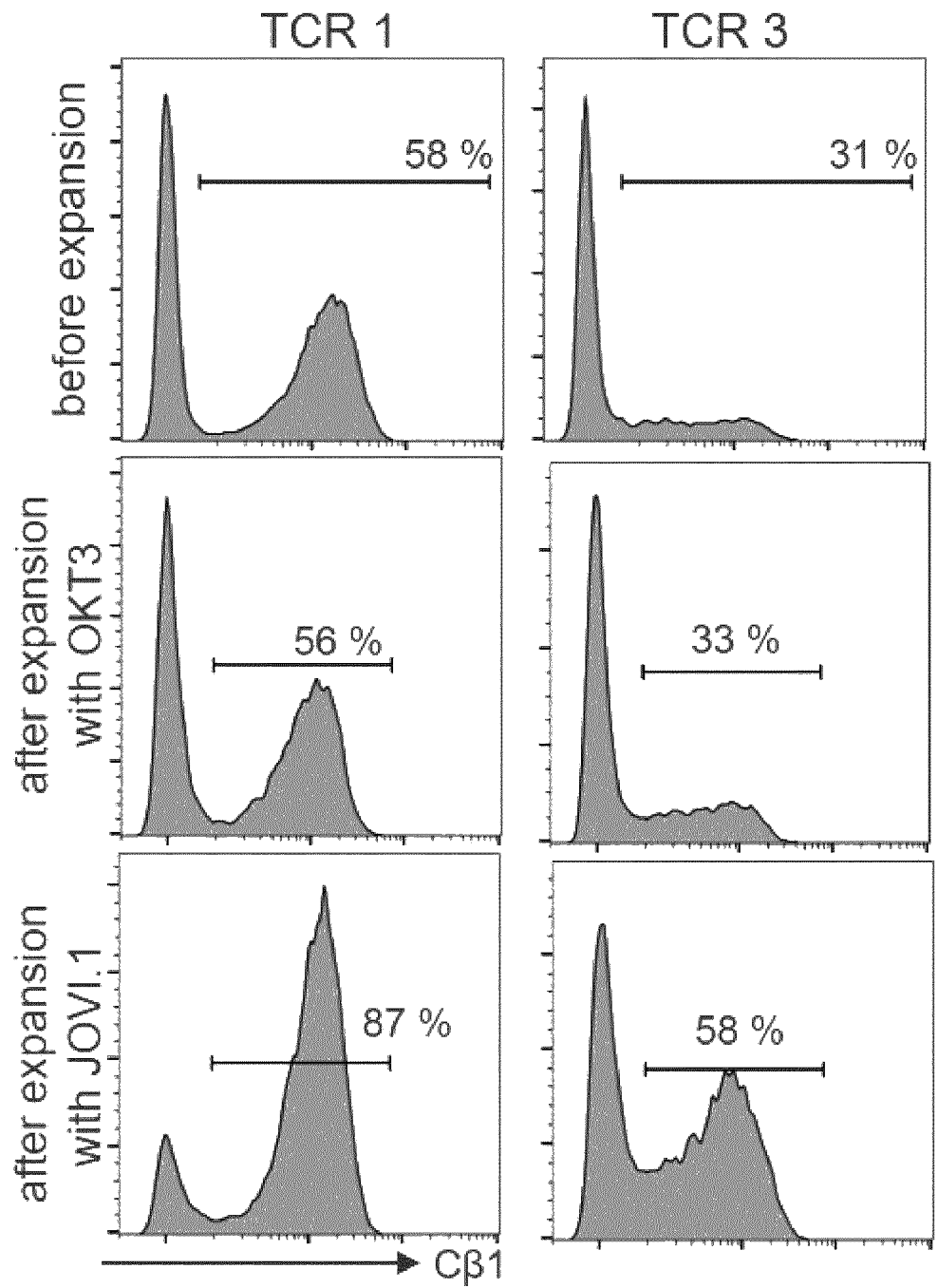

FIG. 6: Specific stimulation of Cβ1-positive TCR-transgenic T cells. Cβ1-depleted CD8-enriched T cells were transduced with two different recombinant TCRs and analyzed for Cβ1-positive cells by flow cytometry. Cells were then expanded by stimulation with either the CD3 antibody OKT3 or JOVI.1 antibody. The specific expansion of Cβ1-positive cells after activation with JOVI.1 antibody was confirmed by flow cytometry.

Figure 7:
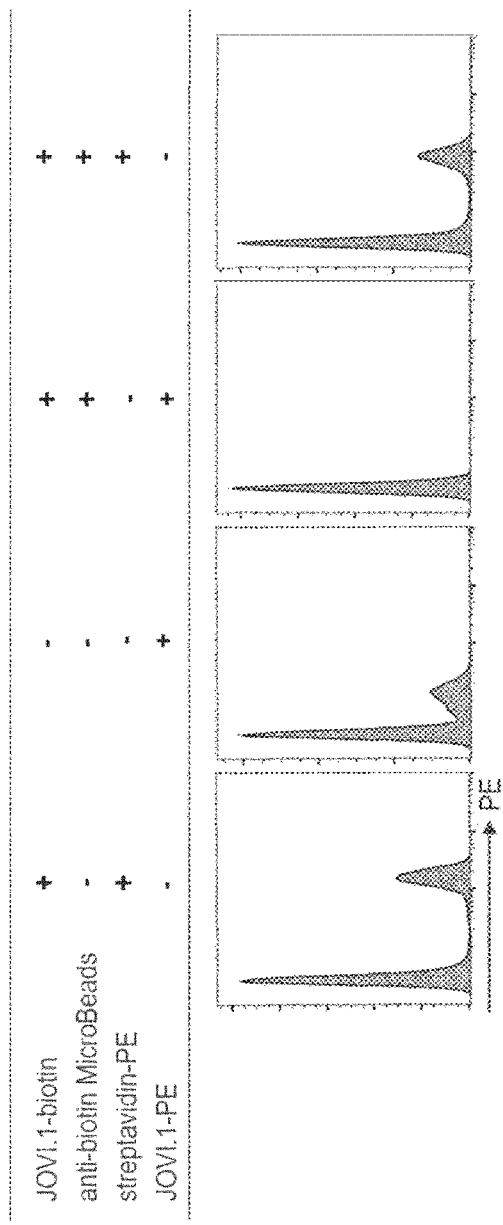

FIG. 7: Comparison of differently tagged variants of JOVI.1 antibody. CD8+ T cells were incubated with different combinations of the following reagents: JOVI.1-biotin antibody, anti-biotin MicroBeads, streptavidin-PE, JOVI.1-PE. Cβ1-positive T cells could be stained with either JOVI.1-biotin/streptavidin-PE or JOVI.1-PE, whereby the staining with JOVI.1-biotin/streptavidin-PE was stronger compared with the JOVI.1-PE staining. After labeling the Cβ1-positive T cells with JOVI.1-biotin and anti-biotin MicroBeads, the cells could be still stained with streptavidin-PE, but not with JOVI.1-PE.

Figure 8:
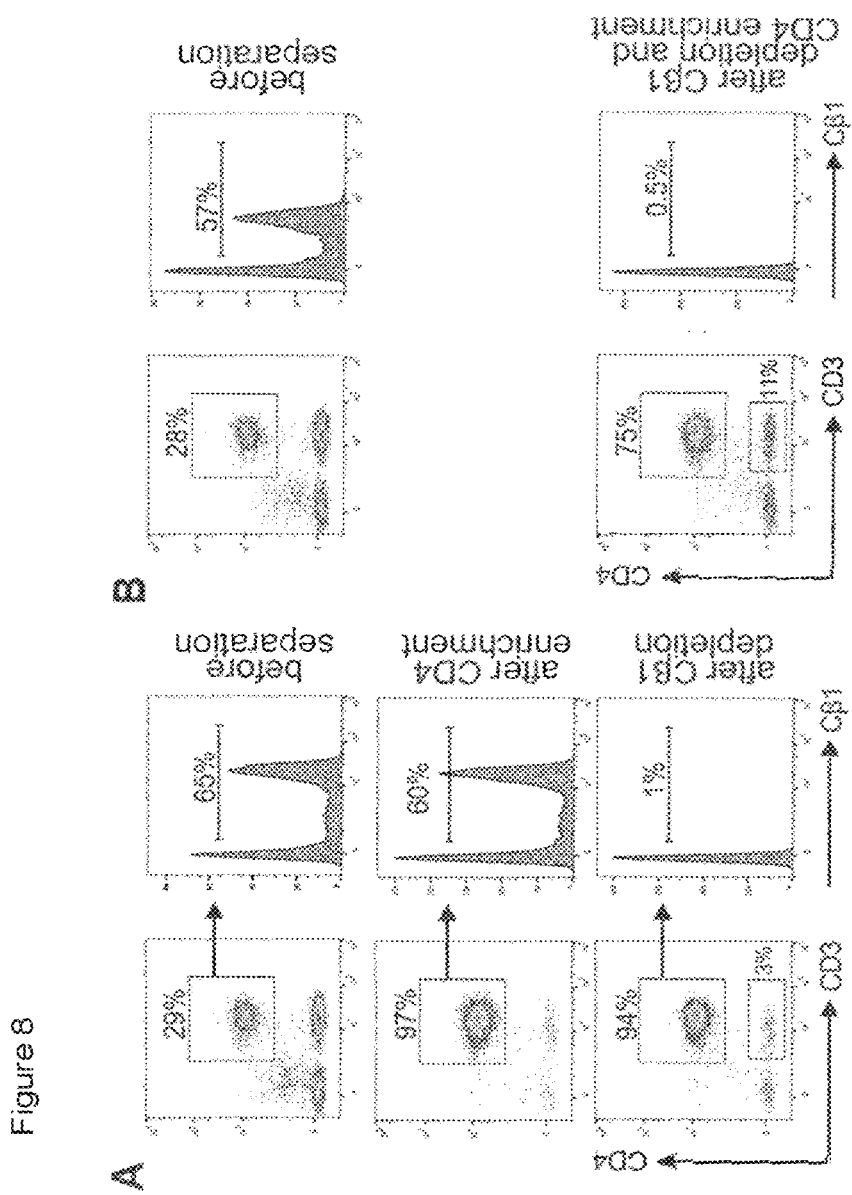

FIG. 8: Enrichment of Cβ1-negative/CD4-positive T cells from CD4 T cells or PBMCs. (A) CD4-positive T cells were enriched from PBMCs by standard protocol and then Cβ1-positive T cells were depleted. Samples were analyzed by flow cytometry for CD3, CD4 and Cβ1 before enrichment, after CD4 enrichment and after Cβ1 depletion. (B) Cβ1-depleted CD4-enriched T cells were isolated in one step from PBMCs. Samples were analyzed by flow cytometry for CD3, CD4 and Cβ1 before enrichment and after Cβ1 depletion and CD4 enrichment.

Figure 9:
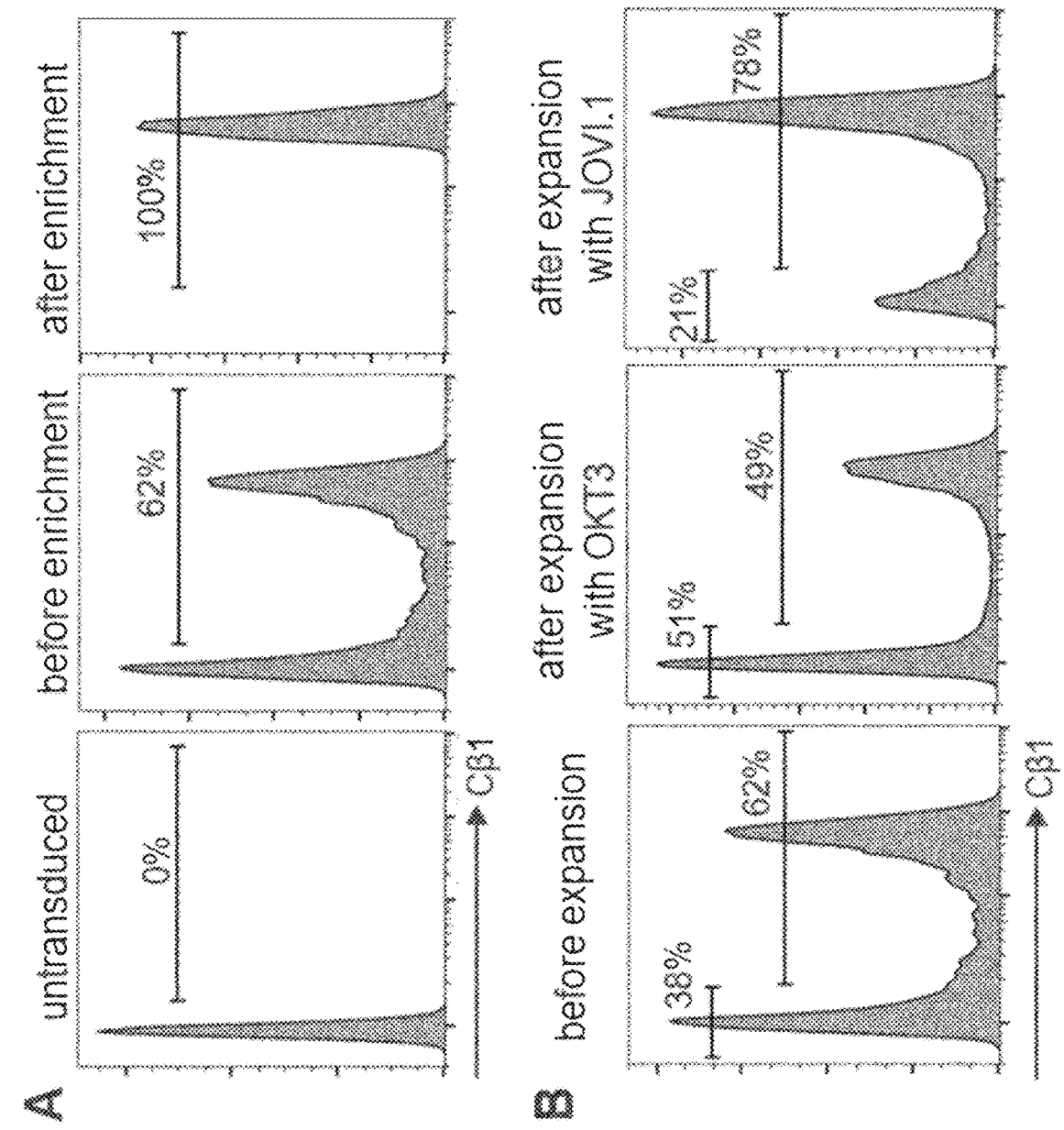

FIG. 9: FACS enrichment and specific stimulation of Cβ1-positive CD4-positive TCR-transgenic T cells. (A) Cβ1-depleted CD4-enriched T cells were transduced with a TCR containing Cβ1. TCR-transgenic T cells were enriched by FACS using JOVI.1 and CD4 monoclonal antibody (mAb). T cells were analyzed by flow cytometry for Cβ1 expression before and after enrichment. Untransduced T cells were used as a control. (B) Cβ1-depleted CD4-enriched T cells were transduced with a TCR containing Cβ1 and analyzed for Cβ1-positive cells by flow cytometry. Cells were then expanded by stimulation with either the CD3 mAb OKT3 or JOVI.1. The specific expansion of Cβ1-positive cells after activation with JOVI.1 was confirmed by flow cytometry.

Figure 10:
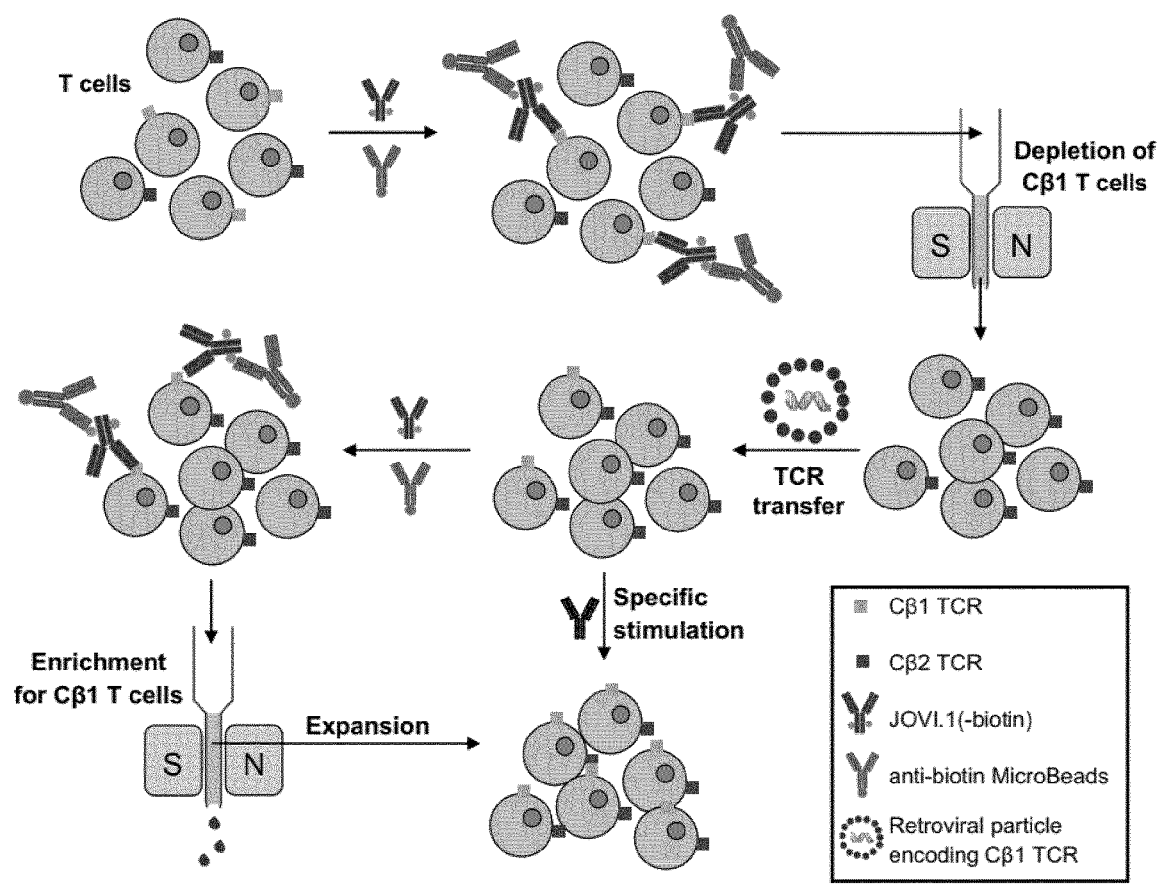

FIG. 10: Concept using JOVI.1 monoclonal antibody to enrich and expand recombinant TCR-expressing T cells. Cβ1-positive T cells can be labeled with a combination of JOVI.1-biotin antibody and anti-biotin MicroBeads and depleted by MACS. The Cβ1-negative T cells can then be transduced with a recombinant TCR containing Cβ1. TCR-expressing transgenic Cβ1-positive T cells can be labeled with a combination of JOVI.1-biotin antibody and anti-biotin MicroBeads and enriched by MACS or they can be enriched by the specific stimulation with JOVI.1 monoclonal antibody.

Figure 11:
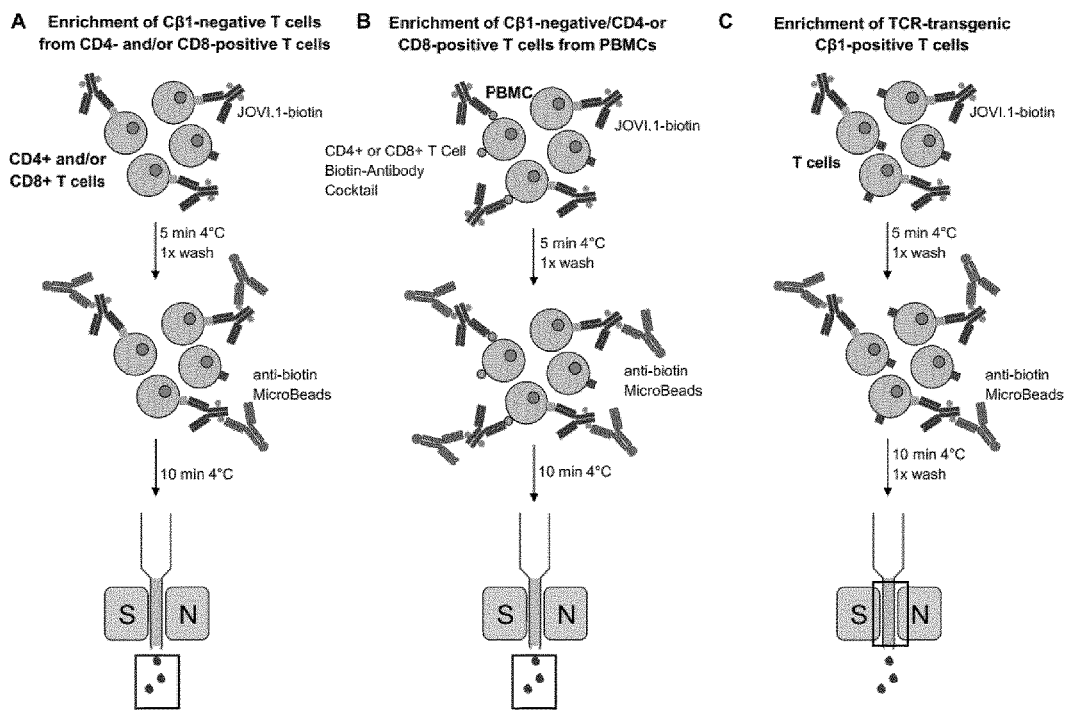

FIG. 11: Schematic of protocols to deplete or enrich Cβ1-positive T cells. (A) Depletion of Cβ1-positive T cells from CD4 and/or CD8 T cells. CD4 and/or CD8 T cells are incubated with JOVI.1-biotin antibody for 5 min at 4° C., washed with MACS buffer, incubated for 10 min at 4° C. with anti-biotin MicroBeads and loaded on a MACS column. The flow through contains the Cβ1-depleted CD4 and/or CD8 T cells. (B) Depletion of Cβ1-positive and enrichment for CD4 or CD8-positive T cells from PBMCs. PBMCs are incubated with JOVI.1-biotin antibody and the "CD4+ T Cell Biotin-Antibody Cocktail" or "CD8+ T Cell Biotin-Antibody Cocktail" (Miltenyi) for 5 min at 4° C., washed with MACS buffer, incubated for 10 min at 4° C. with anti-biotin MicroBeads (Miltenyi) and loaded on a MACS column. The flow through contains the Cβ1-depleted CD4- or CD8-enriched T cells. (C) Enrichment of Cβ1-positive TCR-transgenic T cells. T cells are incubated with JOVI.1-biotin antibody for 5 min at 4° C., washed with MACS buffer, incubated for 10 min at 4° C. with anti-biotin MicroBeads and loaded on a MACS column. Cβ1-positive TCR-transgenic T cells are enriched in the MACS column and can be eluted after removal of the magnet.

DETAILED DESCRIPTION OF THE INVENTION

Before the invention is described in detail with respect to some of its preferred embodiments, the following general definitions are provided.

The present invention as illustratively described in the following may suitably be practiced in the absence of any element or elements, limitation or limitations, not specifically disclosed herein.

The present invention will be described with respect to particular embodiments and with reference to certain figures, but the invention is not limited thereto but only by the claims.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group which preferably consists only of these embodiments.

Where an indefinite or definite article is used when referring to a singular noun, e.g. "a", "an" or "the", this includes a plural of that noun unless something else is specifically stated.

Technical terms are used by their common sense. If a specific meaning is conveyed to certain terms, definitions of terms will be given in the following in the context of which the terms are used.

The present invention provides strategies for generating a T cell population enriched for T cells expressing a recombinant TCR, comprising the steps:
 a) Incubating a composition comprising T cells with an anti-Cβ antibody selected from the group consisting of an anti-Cβ1 antibody and anti-Cβ2 antibody,
 b) Depleting T cells bound to the anti-Cβ antibody,
 c) Introducing into the T cell population obtained in step b) a recombinant TCR containing a Cβ chain to which the anti-Cβ antibody binds,
 d) Enriching T cells expressing the recombinant TCR in the population obtained in step c) using the anti-Cβ antibody.

The term "anti-Cβ antibody" used for the method of the invention is selected from the group consisting of an anti-Cβ1 antibody and anti-Cβ2 antibody. In other words, the anti-Cβ antibody is an antibody which is specific for either the Cβ1 chain (i.e. the anti-Cβ1 antibody binds to the Cβ1 chain of the TCR and does not bind or does substantially not bind to the Cβ2 chain of the TCR) of the TCR or is specific for the Cβ2 of the TCR (i.e. the anti-Cβ2 antibody binds to the Cβ2 chain of the TCR and does not bind or does substantially not bind to the Cβ1 chain of the TCR).

The skilled person understands, that when in step a) anti-Cβ1 antibody is used also steps c) and d) refer to an anti-Cβ1 antibody. Vice versa, when in step b) anti-Cβ2 antibody is used also steps c) and d) refer to an anti-Cβ2 antibody.

In particular, the present invention provides strategies for generating a T cell population enriched for T cells expressing a recombinant TCR, comprising the steps:
 a) Incubating a composition comprising T cells with an anti-Cβ1 antibody,
 b) Depleting T cells bound to the anti-Cβ1 antibody,
 c) Introducing into the T cell population obtained in step b) a recombinant TCR containing a Cβ1 chain,
 d) Enriching T cells expressing the recombinant TCR in the population obtained in step c) using the anti-Cβ1 antibody.

A TCR is composed of two different and separate protein chains, namely the TCR alpha (α) and the TCR beta (β) chain. The TCR α chain comprises variable (V), joining (J) and constant (C) regions. The TCR β chain comprises variable (V), diversity (D), joining (J) and constant (C) regions. The rearranged V(D)J regions of both the TCR α and the TCR β chain contain hypervariable regions (CDR, complementarity determining regions), among which the CDR3 region determines the specific epitope recognition. At the C-terminal region both TCR α chain and TCR β chain contain a hydrophobic transmembrane domain and end in a short cytoplasmic tail.

The constant region of the TCR β chain occurs naturally either in the Cβ1 version or in the Cβ2 version which are typically equally distributed in a population of natural unstimulated T cells.

The anti-Cβ1 antibody may be a monoclonal mouse IgG2a antibody. The skilled person understands that the anti-Cβ1 antibody binds to the Cβ1 chain of the TCR and does not bind or does substantially not bind to the Cβ2 chain of the TCR. In a preferred embodiment, the anti-Cβ1 antibody may comprise a light chain variable region and a heavy chain variable region, wherein the light chain variable region comprises a CDR1 set forth in SEQ ID No: 1, a CDR2 set forth in SEQ ID No: 2, a CDR3 set forth in SEQ ID No: 3; wherein the heavy chain variable region comprises a CDR1 set forth in SEQ ID No: 4, a CDR2 set forth in SEQ ID No: 5 identical thereto, and a CDR3 set forth in SEQ ID No: 6. In a preferred embodiment the anti-Cβ1 antibody is the JOVI.1 antibody, which is commercially available, e.g. from SantaCruz Biotechnology or ThermoFisher Scientific. The sequence of the light chain variable region is set out in SEQ ID NO: 8 and the sequence of the heavy chain variable region is set out in SEQ ID NO: 9. Thus in the method of the application an anti-Cβ1 antibody can be used comprising a light chain and a heavy chain, wherein the light chain variable region and has a sequence which is 75%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 8 and wherein the heavy chain variable region and has a sequence which is 75%, 80%, 81%, 82%, 83%, 84%, 85%, 86%, 87%, 88%, 89%, 90%, 91%, 92%, 93%, 94%, 95%, 96%, 97%, 98%, or 99% identical to SEQ ID NO: 9.

The determination of percent identity between multiple sequences is preferably accomplished using the AlignX application of the Vector NTI Advance™ 10 program (Invitrogen Corporation, Carlsbad CA, USA). This program uses a modified Clustal W algorithm (Thompson et al., 1994. Nucl Acids Res. 22: pp. 4673-4680; Invitrogen Corporation; Vector NTI Advance™ 10 DNA and protein sequence analysis software. User's Manual, 2004, pp. 389-662). The determination of percent identity is performed with the standard parameters of the AlignX application.

The terms "recombinant" and "recombinant TCR" as used in the present application refers to TCRs that have been introduced by any of the genetic engineering techniques into the T cells. The "recombinant TCR" also termed "exogenous TCR" may be engineered or may be a naturally occurring TCR which has a desired antigen specificity and which was isolated. Typically, these recombinant TCRs which were not endogenous to the T cell population, i.e. were not naturally expressed in the T cell population, i.e. were not expressed in the T cell population before transfer of the recombinant TCR.

In some embodiments at least 60%, 65%, 70%, 75%, 80%, 85%, 90%, 95% of the T cell population obtained in step d) express the recombinant TCR.

In some embodiments at least 60%, preferably at least 70%, more preferably at least 80%, most preferably at least 90% of the T cell population obtained in step d) express the recombinant TCR.

That means that after the enrichment of step d) at least 60%, preferably at least 70%, more preferably at least 80%, most preferably at least 90% of T cells of the total population obtained after step d) express the recombinant TCR.

In specific embodiments step d) comprises the steps
 Incubating the cells with an anti-Cβ1 antibody, and
 Isolating the T cells bound to the anti-Cβ1 antibody.
 Optionally step d) further comprises the step of
 Expanding the isolated T cells.

Thus, a specific embodiment refers to a method comprising the steps
 a) Incubating a composition comprising T cells with an anti-Cβ1 antibody,
 b) Depleting T cells bound to the anti-Cβ1 antibody, c) Introducing into the T cell population obtained in step b) a recombinant TCR containing a Cβ1 chain,
d) Enriching T cells expressing the recombinant TCR in the population obtained in step c) using the anti-Cβ1 antibody, comprising the steps
Incubating the cells with an anti-Cβ1 antibody,
Isolating the T cells bound to the anti-Cβ1 antibody,
Expanding the isolated T cells.

For depleting the T cells bound to the anti-Cβ1 antibody any method useful for separating antibody-cell complexes may be used. In particular, sorting techniques such as fluorescent activated cell sorting (FACS) or magnetic-activated cell sorting (MACS) may be used.

The antibody of step a) may be modified to facilitate depletion in step b), e.g. the antibody may be biotinylated. In step b) molecules or complexes binding to the modified antibody may be used, such as anti-biotin Microbeads or Streptavidin-PE.

In a preferred embodiment, a biotinylated anti-Cβ1 antibody is used for the incubation in step a). The depletion then is carried out with a molecule binding to biotin, such as anti-biotin Microbeads. The sorting process is carried out by FACS or MACS. Thereby the complex of T cells comprising the recombinant TCR, the biotinylated anti-Cβ1 antibody and the anti-biotin microbeads is retained on the column, wherein the desired Cβ1 chain negative fraction of T cells are obtained in the flow-through.

In a specific embodiment, a biotinylated anti-Cβ1 antibody is used for the incubation in step a) and the depletion is carried out by MACS with anti-biotin Microbeads.

In another specific embodiment, a biotinylated anti-Cβ1 antibody is used for the incubation in step a) and the depletion is carried out by FACS with Streptavidin-PE.

In a preferred embodiment a biotinylated anti-Cβ1 antibody is used for the enrichment in step d). The isolation of the T cells bound to the anti-Cβ1 antibody is then carried out with anti-biotin microbeads and MACS. Thereby the complex of T cells comprising the recombinant TCR, the biotinylated anti-Cβ1 antibody and the anti-biotin microbeads bound to the column is eluted thereby obtaining the population enriched for T cells comprising the recombinant TCR.

As can be seen from the examples, the claimed method as described is capable of generating T cell populations highly enriched for T cells expressing a recombinant TCR, such as a content of over 90% of T cells expressing a recombinant TCR in the total T cell population after the enrichment of step d).

Alternatively step d) may comprise the step
Incubating the cells with an anti-Cβ1 antibody, wherein the incubation with the anti-Cβ1 antibody stimulates proliferation of T cells expressing the TCR containing a Cβ1 chain.

The introduction of the recombinant TCR containing a Cβ1 chain may occur by any appropriate method known to the skilled person. Typically, the introduction occurs by transduction.

The term "transduction" refers to the process by which an exogenous nucleic acid sequence is introduced into a host cell, e.g. into a T cell. It is noted that introduction or transfer of nucleic acid sequences is not limited to the mentioned methods but can be achieved by any number of means including electroporation, microinjection, gene gun delivery, lipofection, superfection, infection by retroviruses or other suitable viruses for transduction or transfection.

In step c) a nucleic acid encoding a recombinant TCR is typically transduced by a vector into the T cell.

Preferably, in step c) a retroviral particle is used for introducing the TCR.

"Nucleic acid" generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. Preferably, the nucleic acids described herein are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication. The nucleic acids can be constructed based on chemical synthesis and/or enzymatic ligation reactions using procedures known in the art or commercially available (e.g. from Genscript, Thermo Fisher and similar companies). See, for example Sambrook et al., a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). The nucleic acid can comprise any nucleotide sequence which encodes any of the recombinant TCRs, polypeptides, or proteins, or functional portions or functional variants thereof.

The nucleic acid encoding the TCR may be modified. Useful modifications in the overall nucleic acid sequence may be codon optimization. Alterations may be made which lead to conservative substitutions within the expressed amino acid sequence. These variations can be made in complementarity determining and non-complementarity determining regions of the amino acid sequence of the TCR chain that do not affect function. Usually, additions and deletions should not be performed in the CDR3 region.

A "vector" is any molecule or composition that has the ability to carry a nucleic acid sequence into a suitable host cell where synthesis of the encoded polypeptide can take place. Typically, and preferably, a vector is a nucleic acid that has been engineered, using recombinant DNA techniques that are known in the art, to incorporate a desired nucleic acid sequence (e.g. a nucleic acid of the invention). The vector may comprise DNA or RNA and/or comprise liposomes. The vector may be a plasmid, shuttle vector, phagemide, cosmid, expression vector, retroviral vector, lentiviral vector, adenoviral vector or particle. A vector may include nucleic acid sequences that permit it to replicate in a host cell, such as an origin of replication. A vector may also include one or more selectable marker genes and other genetic elements known to those of ordinary skill in the art. A vector preferably is an expression vector that includes a nucleic acid according to the present invention operably linked to sequences allowing for the expression of said nucleic acid.

Preferably, the vector is a retroviral particle.

Usually, the composition comprising T cells comprises a population of T cells expressing a Cβ1 chain and a population of T cells expressing a Cβ2 chain. By the depletion of T cells expressing a Cβ1 chain, a population of Cβ1 chain negative T cells, which are typically T cells expressing a Cβ2 chain, is obtained.

The composition comprising T cells may be obtained from a human.

In some embodiments, the composition comprising T cells comprises peripheral blood lymphocytes (PBL) or peripheral blood mononuclear cells (PBMC). The composition may essentially consist of T cells. The T cell may be a CD4+ or a CD8+ T cell. Preferably, the T cell is a CD8+ T cell.

In some embodiments the cell is a stem cell-like memory T cell. Stem cell-like memory T cells (TSCM) are a less-differentiated subpopulation of CD8+ or CD4+ T cells, which are characterized by the capacity of self-renewal and to persist long-term. Once these cells encounter their antigen in vivo, they differentiate further into central memory T cells (TCM), effector memory T cells (TEM) and terminally differentiated effector memory T cells (TEMRA) with some TSCM remaining quiescent (Flynn et al., Clinical & Translational Immunology (2014)). These remaining TSCM cells show the capacity to build a durable immunological memory in vivo and therefore are considered an important T cell subpopulation for adoptive T cell therapy (Lugli et al., Nature Protocols 8, 33-42 (2013) Gattinoni et al., Nat. Med. 2011 October; 17 (10): 1290-1297). Immune-magnetic selection can be used in order to restrict the T cell pool to the stem cell memory T cell subtype see (Riddell et al. 2014, Cancer Journal 20 (2): 141-44).

Typically, the TCR has a desired antigen-specificity. This means that the TCR is selected because it binds to a specific antigen or to a specific epitope. The TCR may be engineered in order to exhibit a desired antigen-specificity. For example, the variable chain, in particular the CDR1, CDR2 or CDR3 are engineered in order to bind to a specific antigen.

Another aspect refers to the use of an anti-Cβ1 antibody for the enrichment of T cells expressing a recombinant TCR.

By the term antibody also binding fragments of said antibody are included.

Binding fragments may include portions of an intact full-length antibody, such as an antigen binding or variable region of the complete antibody. Examples of antibody fragments include Fab, F(ab')2, Id and Fv fragments; diabodies; linear antibodies; single-chain antibody molecules (e.g., scFv); multispecific antibody fragments such as bispecific, trispecific, and multispecific antibodies (e.g., diabodies, triabodies, tetrabodies); minibodies; chelating recombinant antibodies; tribodies or bibodies; intrabodies; nanobodies; small modular immunopharmaceuticals (SMIP), binding-domain immunoglobulin fusion proteins; camelized antibodies; VHH containing antibodies); and any other polypeptides formed from antibody fragments. The skilled person is aware that the antigen-binding function of an antibody can be performed by fragments of a full-length antibody. Preferably, the binding fragment is a Fab fragment.

A Fab fragment consists of the VL, VH, CL and CH1 domains. An F(ab')2 fragment comprises two Fab fragments linked by a disulfide bridge at the hinge region. An Fd is the VH and CH1 domains of a single arm of an antibody. An Fv fragment is the VL and VH domains of a single arm of an antibody.

The method and the use explained in detail above employing anti-Cβ1 antibody also applies to an anti-Cβ2 antibody (i.e. an antibody binds to Cβ2 and that does substantially not bind to Cβ1) which can be used for the enrichment of a TCR comprising a Cβ2 chain. Thus, the present invention also provides strategies for generating a T cell population enriched for T cells expressing a recombinant TCR, comprising the steps:

a) Incubating a composition comprising T cells with an anti-Cβ2 antibody,
b) Depleting T cells bound to the anti-Cβ2 antibody,
c) Introducing into the T cell population obtained in step b) a recombinant TCR containing a Cβ2 chain,
d) Enriching T cells expressing the recombinant TCR in the population obtained in step c) using the anti-Cβ2 antibody.

Thus, as already stated above, in more general terms, the present invention provides strategies for generating a T cell population enriched for T cells expressing a recombinant TCR, comprising the steps:

a) Incubating a composition comprising T cells with an anti-Cβ antibody selected from the group consisting of an anti-Cβ1 antibody and anti-Cβ2 antibody,
b) Depleting T cells bound to the anti-Cβ antibody,
c) Introducing into the T cell population obtained in step b) a recombinant TCR containing a Cβ chain to which the anti-Cβ antibody binds,
d) Enriching T cells expressing the recombinant TCR in the population obtained in step c) using the anti-Cβ antibody.

The invention also refers to a kit comprising
a nucleotide acid encoding a TCR containing a Cβ1 chain, and
an anti-Cβ1 antibody.

In one embodiment the kit comprises
a)
an anti-Cβ1 antibody,
a nucleotide acid encoding a TCR containing a Cβ1 chain to which the anti-Cβ1 antibody binds, and/or
b)
an anti-Cβ2 antibody,
a nucleotide acid encoding a TCR containing a Cβ2 chain to which the anti-Cβ2 antibody binds.

EXAMPLES

Enrichment of Cβ1-Negative/CD8-Positive T Cells
Enrichment of Cβ1-Negative T Cells from CD8-Positive T Cells CD8-positive T cells (enriched from PBMCs by standard protocol) were depleted for Cβ1-positive T cells. CD8 T cells are incubated with JOVI.1-biotin antibody (15 µl/$10^7$ cells, c=1 mg/ml) for 5 min at 4° C., washed with MACS buffer, incubated for 10 min at 4° C. with anti-biotin MicroBeads (20 µl/$10^7$ cells) and loaded on a MACS column. The flow through contains the Cβ1-depleted CD8 T cells. Samples were analyzed by flow cytometry for CD3, CD8 and Cβ1 before enrichment, after CD8 enrichment and after Cβ1 depletion. (FIG. 3A).

Enrichment of Cβ1-Negative/CD8-Positive T Cells from PBMCs

Cβ1-depleted CD8-enriched T cells were isolated in one step from PBMCs. PBMCs are incubated with JOVI.1-biotin antibody (5 µl/$10^7$ cells, c=1 mg/ml) and the "CD8+ T Cell Biotin-Antibody Cocktail" (Miltenyi, 10 µl/$10^7$ cells) for 5 min at 4° C., washed with MACS buffer, incubated for 10 min at 4° C. with anti-biotin MicroBeads (Miltenyi, 20 µl/$10^7$ cells) and loaded on a MACS column. The flow through contains the Cβ1-depleted CD8-enriched T cells. Samples were analyzed by flow cytometry for CD3, CD8 and Cβ1 before enrichment and after Cβ1 depletion and CD8 enrichment. (FIG. 3B)

MACS Enrichment of Cβ1-Positive TCR-Transgenic T Cells

Cβ1-depleted CD8-enriched T cells were transduced with three different recombinant TCRs. TCR-transgenic T cells were enriched by MACS using JOVI.1 antibody and expanded. In particular, T cells are incubated with JOVI.1-biotin antibody (15 μl/$10^7$ cells, c=1 mg/ml) for 5 min at 4° C., washed with MACS buffer, incubated for 10 min at 4° C. with anti-biotin MicroBeads (20 μl/$10^7$ cells) and loaded on a MACS column. Cβ1-positive TCR-transgenic T cells are enriched in the MACS column and can be eluted after removal of the magnet. T cells were analyzed by flow cytometry for Cβ1 expression before enrichment, after enrichment and after expansion. (FIG. 4)

FACS Enrichment of Cβ1-Positive CD8-Positive TCR-Transgenic T Cells

Cβ1-depleted CD8-enriched T cells were transduced with six different recombinant TCRs. TCR-transgenic T cells were enriched by FACS using JOVI.1 mAb and CD8 mAb and expanded. In particular, T cells are incubated with JOVI.1-biotin antibody (15 μl/$10^7$ cells, c=1 mg/ml) for 5 min at 4° C. and washed with FACS buffer. Then, the cells were incubated with Streptavidin-PE for 5 min at 4° C., washed with FACS buffer and FACS sorted. T cells were analyzed by flow cytometry for Cβ1 and CD8 expression before enrichment and after enrichment and expansion. (FIG. 5)

Specific Stimulation of Cβ1-Positive TCR-Transgenic T Cells

Cβ1-depleted CD8-enriched T cells were transduced with two different recombinant TCRs and analyzed for Cβ1-positive cells by flow cytometry. Cells were then expanded by stimulation with either the CD3 mAb OKT3 or JOVI.1 mAb. The specific expansion of Cβ1-positive cells after activation with JOVI.1 mAb was confirmed by flow cytometry. (FIG. 6)

Enrichment of Cβ1-Negative T Cells from CD4-Positive T Cells

CD4-positive T cells (enriched from PBMCs by standard protocol) were depleted for Cβ1-positive T cells. CD4 T cells are incubated with JOVI.1-biotin antibody (15 μl/$10^7$ cells, c=1 mg/ml) for 5 min at 4° C., washed with MACS buffer, incubated for 10 min at 4° C. with anti-biotin MicroBeads (20 μl/$10^7$ cells) and loaded on a MACS column. The flow through contains the Cβ1-depleted CD4 T cells. Samples were analyzed by flow cytometry for CD3, CD4 and Cβ1 before enrichment, after CD4 enrichment and after Cβ1 depletion. (FIG. 8A)

Enrichment of Cβ1-Negative/CD4-Positive T Cells from PBMCs

Cβ1-depleted CD4-enriched T cells were isolated in one step from PBMCs. PBMCs are incubated with JOVI.1-biotin antibody (5 μl/$10^7$ cells, c=1 mg/ml) and the "CD4+ T Cell Biotin-Antibody Cocktail" (Miltenyi, 10 μl/$10^7$ cells) for 5 min at 4° C., washed with MACS buffer, incubated for 10 min at 4° C. with anti-biotin MicroBeads (Miltenyi, 20 μl/$10^7$ cells) and loaded on a MACS column. The flow through contains the Cβ1-depleted CD4-enriched T cells. Samples were analyzed by flow cytometry for CD3, CD4 and Cβ1 before enrichment and after Cβ1 depletion and CD4 enrichment. (FIG. 8B)

FACS Enrichment of Cβ1-Positive CD4-Positive TCR-Transgenic T Cells

Cβ1-depleted CD4-enriched T cells were transduced with a recombinant TCR containing Cβ1. TCR-transgenic T cells were enriched by FACS using JOVI.1 mAb and CD4 mAb. In particular, T cells are incubated with JOVI.1-biotin antibody (15 μl/$10^7$ cells, c=1 mg/ml) for 5 min at 4° C. and washed with FACS buffer. Then, the cells were incubated with Streptavidin-PE for 5 min at 4° C., washed with FACS buffer and FACS sorted. T cells were analyzed by flow cytometry for Cβ1 and CD4 expression before enrichment and after enrichment in comparison to untransduced T cells. (FIG. 9A)

Specific Stimulation of Cβ1-Positive TCR-Transgenic T Cells

To show, that T cells expressing a TCR containing Cβ1 can be specifically stimulated, TCR-transduced T cells were activated using the JOVI.1 mAb in comparison to the unspecific stimulation with the anti-CD3 mAb OKT3. In particular, Cβ1-depleted CD4-enriched T cells were transduced with a recombinant TCR containing Cβ1 and analyzed for Cβ1-positive cells by flow cytometry. Cells were then expanded by stimulation with either OKT3 or JOVI.1 mAb. Cβ1-positive cells were specifically expanded after activation with JOVI.1 mAb as the fraction of Cβ1-positive T cells increased compared to the unspecific stimulation with OKT3. (FIG. 9B)

The invention further comprises the following items:

Item 1: In vitro method for generation of a T cell population enriched for T cells expressing a recombinant T cell receptor (TCR) comprising the steps:
  a) Incubating a composition comprising T cells with an anti-Cβ antibody selected from the group consisting of an anti-Cβ1 antibody and anti-Cβ2 antibody,
  b) Depleting T cells bound to the anti-Cβ antibody,
  c) Introducing into the T cell population obtained in step b) a recombinant TCR containing a Cβ chain to which the anti-Cβ antibody binds,
  d) Enriching T cells expressing the recombinant TCR in the population obtained in step c) using the anti-Cβ antibody.

Item 2: Method according to item 1, wherein at least 60%, preferably at least 70% more preferably at least 80%, most preferably at least 90% of the T cell population obtained in step d) express the recombinant TCR.

Item 3: Method according to any one of item 1 or 2, wherein step d) comprises the steps
  Incubating the cells with the anti-Cβ antibody, and
  Isolating the T cells bound to the anti-Cβ antibody.

Item 4: Method according to item 3, wherein step d) further comprises the step of
  Expanding the isolated T cells.

Item 5: Method according to any one of item 1 or 2, wherein step d) comprises the step
  Incubating the cells with the anti-Cβ antibody, wherein the incubation with the anti-Cβ antibody stimulates proliferation of T cells expressing the TCR containing a Cβ chain to which the anti-Cβ antibody binds.

Item 6: Method according to any one of the preceding items, wherein in step c) a retroviral particle is used for introducing the TCR.

Item 7: Method according to any one of the preceding items, wherein the composition comprising T cells comprises a population of T cells expressing a Cβ1 chain and a population of T cells expressing a Cβ2 chain.

Item 8: Method according to any one of the preceding items, wherein the composition comprising T cells is obtained from a human.

Item 9: Method according to any one of the preceding items, wherein the composition comprising T cells comprises PBMCs.

Item 10: Method according to any one of the preceding items, wherein the TCR has a desired antigen-specificity.

Item 11: Method according to any one of the preceding items, wherein the T cell is a CD8+ T-cell.

Item 12: Method according to any one items 1 to 10, wherein the T cell is a CD4+ T-cell.

Item 13: Method according to any one of the preceding items, wherein the anti-Cβ antibody of step a) is biotinylated.

Item 14: Method according to item 12, wherein in step b) anti-biotin MicroBeads are used.

Item 15: Method according any one of items 3 or 4, wherein in step d) the anti-Cβ antibody is biotinylated and wherein anti-biotin MicroBeads are used for isolating the T cells bound to the anti-Cβ antibody.

Item 16: Method according to any one of the preceding items, wherein the anti-Cβ antibody is an anti-Cβ1 antibody and the recombinant TCR containing a Cβ chain contains a Cβ1 chain.

Item 17: Method according to any one of the preceding items, wherein the anti-Cβ1 antibody comprises a light chain variable region and a heavy chain variable region, wherein the light chain variable region comprises a CDR1 set forth in SEQ ID No: 1, a CDR2 set forth in SEQ ID No: 2, a CDR3 set forth in SEQ ID No: 3; wherein the heavy chain variable region comprises a CDR1 set forth in SEQ ID No: 4, a CDR2 set forth in SEQ ID No: 5 identical thereto, and a CDR3 set forth in SEQ ID No: 6.

Item 18: Method according to item 17, wherein the anti-Cβ1 antibody comprises light chain variable region having an amino acid sequence set out in SEQ ID NO: 8 and the sequence of the heavy chain variable region is set out in SEQ ID NO: 9.

Item 19: Method according to any one of the preceding items, wherein the anti-Cβ1 antibody is JOVI.1.

Item 20: Use of an anti-Cβ antibody for the enrichment of T cells expressing a recombinant TCR, wherein the anti-Cβ antibody is selected from the group consisting of an anti-Cβ1 antibody and anti-Cβ2 antibody.

Item 21: Method according to item 1 comprising the steps:
a) Incubating a composition comprising T cells with an anti-Cβ1 antibody,
b) Depleting T cells bound to the anti-Cβ1 antibody,
c) Introducing into the T cell population obtained in step b) a recombinant TCR containing a Cβ1 chain,
d) Enriching T cells expressing the recombinant TCR in the population obtained in step c) using the anti-Cβ1 antibody.

Item 22. Method according to item 21, wherein at least 60%, preferably at least 70% more preferably at least 80%, most preferably at least 90% of the T cell population obtained in step d) express the recombinant TCR.

Item 23: Method according to any one of claim 21 or 22, wherein step d) comprises the steps
Incubating the cells with an anti-Cβ1 antibody, and
Isolating the T cells bound to the anti-Cβ1 antibody.

Item 24: Method according to claim 23, wherein step d) further comprises the step of
Expanding the isolated T cells.

Item 25: Method according to any one of claim 21 or 22, wherein step d) comprises the step
Incubating the cells with an anti-Cβ1 antibody, wherein the incubation with the anti-Cβ1 antibody stimulates proliferation of T cells expressing the TCR containing a Cβ1 chain.

Item 26: Method according to any one of items 20 to 25, wherein in step c) a retroviral particle is used for introducing the TCR.

Item 27. Method according to any one of items 20 to 26, wherein the composition comprising T cells comprises a population of T cells expressing a Cβ1 chain and a population of T cells expressing a Cβ2 chain.

Item 28. Method according to any one of items 20 to 27, wherein the composition comprising T cells is obtained from a human.

Item 29. Method according to any one of items 20 to 28, wherein the composition comprising T cells comprises PBMCs.

Item 30. Method according to any one of items 20 to 29, wherein the TCR has a desired antigen-specificity.

Item 31. Method according to any one of items 20 to 30, wherein the T cell is a CD8+ T-cell.

Item 32. Method according to any one of items 20 to 30, wherein the T cell is a CD4+ T-cell.

Item 33. Method according to any one of items 20 to 31, wherein the anti-Cβ1 antibody of step a) is biotinylated.

Item 34. Method according to item 33, wherein in step b) anti-biotin MicroBeads are used.

Item 35. Method according any one of items 23 or 24, wherein in step d) the anti-Cβ1 antibody is biotinylated and wherein anti-biotin MicroBeads are used for isolating the T cells bound to the anti-Cβ1 antibody.

Item 36: Method according to any one of items 20 to 35, wherein the anti-Cβ1 antibody comprises a light chain variable region and a heavy chain variable region, wherein the light chain variable region comprises a CDR1 set forth in SEQ ID No: 1, a CDR2 set forth in SEQ ID No: 2, a CDR3 set forth in SEQ ID No: 3; wherein the heavy chain variable region comprises a CDR1 set forth in SEQ ID No: 4, a CDR2 set forth in SEQ ID No: 5 identical thereto, and a CDR3 set forth in SEQ ID No: 6.

Item 37: Method according to item 36, wherein the anti-Cβ1 antibody comprises light chain variable region having an amino acid sequence set out in SEQ ID NO: 8 and the sequence of the heavy chain variable region is set out in SEQ ID NO: 9.

Item 38. Method according to any one of items 37, wherein the anti-Cβ1 antibody is JOVI.1.

Item 39. Use of an anti-Cβ1 antibody for the enrichment of T cells expressing a recombinant TCR.

Item 40. Kit comprising
an anti-Cβ antibody,
a nucleotide acid encoding a TCR containing a Cβ chain to which the anti-Cβ antibody binds.

The invention claimed is:

1. An in vitro method for generation of a T cell population enriched for T cells expressing a recombinant T cell receptor (TCR) comprising the steps:
   a) Incubating a composition comprising T cells with an anti-Cβ antibody selected from the group consisting of an anti-Cβ1 antibody and anti-Cβ2 antibody,
   b) Depleting T cells bound to the anti-Cβ antibody,
   c) Introducing into the T cell population obtained in step b) a recombinant TCR containing a Cβ chain to which the anti-Cβ antibody binds,
   d) Enriching T cells expressing the recombinant TCR in the population obtained in step c) using the anti-Cβ antibody.

2. The method according to claim 1, wherein at least 60% of the T cell population obtained in step d) express the recombinant TCR.

3. The method according to claim 1, wherein step d) comprises the steps
   Incubating the cells with the Cβ antibody, and
   Isolating the T cells bound to the anti-Cβ antibody.

4. The method according to claim 3, wherein in step d) the anti-Cβ antibody is biotinylated and wherein anti-biotin MicroBeads are used for isolating the T cells bound to the anti-Cβ antibody.

5. The method according to claim 3, wherein step d) further comprises the step of
   Expanding the isolated T cells.

6. The method according to claim 1, wherein step d) comprises the step
   Incubating the cells with the anti-Cβ antibody, wherein the incubation with the anti-Cβ antibody stimulates proliferation of T cells expressing the TCR containing a Cβ chain to which the anti-Cβ antibody binds.

7. The method according to claim 1, wherein in step c) a retroviral particle is used for introducing the TCR.

8. The method according to claim 1, wherein the composition comprising T cells comprises a population of T cells expressing a Cβ1 chain and a population of T cells expressing a Cβ2 chain.

9. The method according to claim 1, wherein the composition comprising T cells is obtained from a human.

10. The method according to claim 1, wherein the composition comprising T cells comprises PBMCs.

11. The method according to claim 1, wherein the TCR has a desired antigen-specificity.

12. The method according to claim 1, wherein the T cell is a CD8+ T-cell or a CD4+ T-cell.

13. The method according to claim 1, wherein the anti-Cβ antibody of step a) is biotinylated.

14. The method according to claim 13, wherein in step b) anti-biotin MicroBeads are used.

15. The method according to claim 1, wherein the anti-Cβ antibody is an anti-Cβ1 antibody.

16. The method according to claim 1, wherein the anti-Cβ1 antibody is JOVI.1.

* * * * *

UNITED STATES PATENT AND TRADEMARK OFFICE
CERTIFICATE OF CORRECTION

| | | |
|---|---|---|
| PATENT NO. | : 12,173,318 B2 | Page 1 of 1 |
| APPLICATION NO. | : 18/020303 | |
| DATED | : December 24, 2024 | |
| INVENTOR(S) | : Sommermeyer et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 24 days.

Signed and Sealed this
Twelfth Day of August, 2025

Coke Morgan Stewart
*Acting Director of the United States Patent and Trademark Office*

SEQUENCE LISTING

<160> NUMBER OF SEQ ID NOS: 10

<210> SEQ ID NO 1
<211> LENGTH: 16
<212> TYPE: PRT
<213> ORGANISM: Artificial Sequence

```
<220> FEATURE:
<223> OTHER INFORMATION: JOVI.1 CDR1 light chain

<400> SEQUENCE: 1

Arg Ser Ser Gln Arg Leu Val His Ser Asn Gly Asn Thr Tyr Leu His
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: JOVI.1 CDR2 light chain

<400> SEQUENCE: 2

Arg Val Ser Asn Arg Phe Pro
1               5

<210> SEQ ID NO 3
<211> LENGTH: 8
<212> TYPE: PRT
<213> ORGANISM: Artificial Sequence
<220> FEATURE:
<223> OTHER INFORMATION: JOVI.1 CDR3 light chain

<400> SEQUENCE: 3

Ser Gln Ser Thr His Val Pro Tyr
1               5

<210> SEQ ID NO 4
<211> LENGTH: 7
<212> TYPE: PRT
<213> ORGANISM: Artificial Sequence
<220> FEATURE:
<223> OTHER INFORMATION: JOVI.1 CDR1 heavy chain

<400> SEQUENCE: 4

Gly Tyr Thr Phe Thr Gly Tyr
1               5

<210> SEQ ID NO 5
<211> LENGTH: 6
<212> TYPE: PRT
<213> ORGANISM: Artificial Sequence
<220> FEATURE:
<223> OTHER INFORMATION: JOVI.1 CDR2 heavy chain

<400> SEQUENCE: 5

Asn Pro Tyr Asn Asp Asp
1               5

<210> SEQ ID NO 6
<211> LENGTH: 15
<212> TYPE: PRT
<213> ORGANISM: Artificial Sequence
<220> FEATURE:
<223> OTHER INFORMATION: JOVI.1 CDR3  heavy chain

<400> SEQUENCE: 6

Gly Ala Gly Tyr Asn Phe Asp Gly Ala Tyr Arg Phe Phe Asp Phe
1               5                   10                  15

<210> SEQ ID NO 7
<211> LENGTH: 113
<212> TYPE: PRT
<213> ORGANISM: Artificial Sequence
<220> FEATURE:
```

<223> OTHER INFORMATION: JOVI.1 light chain variable region

<400> SEQUENCE: 7

Asp Val Val Met Thr Gln Ser Pro Leu Ser Leu Pro Val Ser Leu Gly
1               5                   10                  15

Asp Gln Ala Ser Ile Ser Cys Arg Ser Ser Gln Arg Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Arg Val Ser Asn Arg Phe Pro Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Ser
                85                  90                  95

Thr His Val Pro Tyr Thr Phe Gly Gly Gly Thr Lys Leu Glu Ile Lys
            100                 105                 110

Arg

<210> SEQ ID NO 8
<211> LENGTH: 124
<212> TYPE: PRT
<213> ORGANISM: Artificial Sequence
<220> FEATURE:
<223> OTHER INFORMATION: JOVI.2 heavy chain variable region

<400> SEQUENCE: 8

Glu Val Arg Leu Gln Gln Ser Gly Pro Asp Leu Ile Lys Pro Gly Ala
1               5                   10                  15

Ser Val Lys Met Ser Cys Lys Ala Ser Gly Tyr Thr Phe Thr Gly Tyr
            20                  25                  30

Val Met His Trp Val Lys Gln Arg Pro Gly Gln Gly Leu Glu Trp Ile
        35                  40                  45

Gly Phe Ile Asn Pro Tyr Asn Asp Ile Gln Ser Asn Glu Arg Phe
    50                  55                  60

Arg Gly Lys Ala Thr Leu Thr Ser Asp Lys Ser Ser Thr Thr Ala Tyr
65                  70                  75                  80

Met Glu Leu Ser Ser Leu Thr Ser Glu Asp Ser Ala Val Tyr Tyr Cys
                85                  90                  95

Ala Arg Gly Ala Gly Tyr Asn Phe Asp Gly Ala Tyr Arg Phe Phe Asp
            100                 105                 110

Phe Trp Gly Gln Gly Thr Thr Leu Thr Val Ser Ser
        115                 120

<210> SEQ ID NO 9
<211> LENGTH: 176
<212> TYPE: PRT
<213> ORGANISM: Artificial Sequence
<220> FEATURE:
<223> OTHER INFORMATION: Cbeta1

<400> SEQUENCE: 9

Asp Leu Asn Lys Val Phe Pro Pro Glu Val Ala Val Phe Glu Pro Ser
1               5                   10                  15

Glu Ala Glu Ile Ser His Thr Gln Lys Ala Thr Leu Val Cys Leu Ala
            20                  25                  30

Thr Gly Phe Phe Pro Asp His Val Glu Leu Ser Trp Trp Val Asn Gly
        35                  40                  45

Lys Glu Val His Ser Gly Val Ser Thr Asp Pro Gln Pro Leu Lys Glu
            50                  55                  60

Gln Pro Ala Leu Asn Asp Ser Arg Tyr Cys Leu Ser Ser Arg Leu Arg
 65                  70                  75                  80

Val Ser Ala Thr Phe Trp Gln Asn Pro Arg Asn His Phe Arg Cys Gln
                 85                  90                  95

Val Gln Phe Tyr Gly Leu Ser Glu Asn Asp Glu Trp Thr Gln Asp Arg
                100                 105                 110

Ala Lys Pro Val Thr Gln Ile Val Ser Ala Glu Ala Trp Gly Arg Ala
                115                 120                 125

Asp Cys Gly Phe Thr Ser Val Ser Tyr Gln Gln Gly Val Leu Ser Ala
                130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Phe
                165                 170                 175

<210> SEQ ID NO 10
<211> LENGTH: 178
<212> TYPE: PRT
<213> ORGANISM: Artificial Sequence
<220> FEATURE:
<223> OTHER INFORMATION: Cbeta2

<400> SEQUENCE: 10

Asp Leu Lys Asn Val Phe Pro Pro Glu Val Ala Val Phe Glu Pro Ser
 1               5                  10                  15

Glu Ala Glu Ile Ser His Thr Gln Lys Ala Thr Leu Val Cys Leu Ala
                 20                  25                  30

Thr Gly Phe Tyr Pro Asp His Val Glu Leu Ser Trp Trp Val Asn Gly
                 35                  40                  45

Lys Glu Val His Ser Gly Val Ser Thr Asp Pro Gln Pro Leu Lys Glu
            50                  55                  60

Gln Pro Ala Leu Asn Asp Ser Arg Tyr Cys Leu Ser Ser Arg Leu Arg
 65                  70                  75                  80

Val Ser Ala Thr Phe Trp Gln Asn Pro Arg Asn His Phe Arg Cys Gln
                 85                  90                  95

Val Gln Phe Tyr Gly Leu Ser Glu Asn Asp Glu Trp Thr Gln Asp Arg
                100                 105                 110

Ala Lys Pro Val Thr Gln Ile Val Ser Ala Glu Ala Trp Gly Arg Ala
                115                 120                 125

Asp Cys Gly Phe Thr Ser Glu Ser Tyr Gln Gln Gly Val Leu Ser Ala
                130                 135                 140

Thr Ile Leu Tyr Glu Ile Leu Leu Gly Lys Ala Thr Leu Tyr Ala Val
145                 150                 155                 160

Leu Val Ser Ala Leu Val Leu Met Ala Met Val Lys Arg Lys Asp Ser
                165                 170                 175

Arg Gly